United States Patent [19]

Suwa et al.

[11] Patent Number: 4,867,990

[45] Date of Patent: Sep. 19, 1989

[54] FOOD AND BEVERAGES CONTAINING LACTATE MONOOXYGENASE

[75] Inventors: Yoshihide Suwa, Osaka; Takumi Kobayashi, Kanagawa; Hiroshi Ishigouoka, Kyoto; Miyoko Ono, Osaka, all of Japan

[73] Assignee: Suntory Limited, Osaka, Japan

[21] Appl. No.: 232,845

[22] Filed: Aug. 16, 1988

[30] Foreign Application Priority Data

Aug. 17, 1987 [JP] Japan .................................. 62-203892

[51] Int. Cl.⁴ .......................... A23C 9/12; A23F 3/10; A23F 5/00; C12G 3/00

[52] U.S. Cl. .......................................... 426/8; 426/11; 426/15; 426/16; 426/42; 426/45; 426/52; 426/61

[58] Field of Search ...................... 426/8, 9, 10, 11, 12, 426/15, 16, 42, 52, 56, 45, 61

[56] References Cited

U.S. PATENT DOCUMENTS 3,920,521 11/1975 Michelson et al. ................... 426/61

Primary Examiner—Marianne Cintins
Attorney, Agent, or Firm—Cushman, Darby & Cushman

[57] ABSTRACT

Foods or beverages in which lactate monooxygenase is incorporated so as to prevent oxygen-caused deterioration of their quality by allowing oxygen to be eliminated from said foods or beverages rapidly and in a safe way.

11 Claims, 4 Drawing Sheets

FOOD AND BEVERAGES CONTAINING LACTATE MONOOXYGENASE

BACKGROUND OF THE INVENTION

1. Field of the Invention

The present invention relates to foods and beverages containing lactate monooxygenase. Foods, beverages and various table luxuries (hereinafter collectively referred to as foods and beverages) deteriorate in quality during distribution and storage. One major cause of this problem is that even if foods and beverages are sealed in containers, they are subject to oxidative deterioration, i.e., direct or indirect oxidation of their components by oxygen that is present in the head space of the container or dissolved in the contents. The present invention is principally intended to provide foods and beverages in which lactate monooxygenase is incorporated so as to prevent deterioration of their quality by causing oxygen to be eliminated therefrom rapidly and in a safe way.

Browning, which is one of the forms of oxygenassociated deterioration of foods and beverages, is known to involve the reaction that accompanies oxidation of ascorbic acid and the reaction caused by phenolase. In the former reaction, browning is triggered by oxidation of ascorbic acid, which is promoted either by direct oxidation with dissolved oxygen or by the catalytic action of ascorbate oxidase. In the second type of reaction which involves phenolase, oxygen participates in the reaction as a substrate whether the phenolase is cresolase which hydroxylates monophenols or catecholase which accelerates the oxidation of diphenol that is produced by the action of cresolase. The oxidation caused by either mechanism causes many of the food components to become involved in various chain reactions including nonenzymatic reactions such as the Maillard reaction, thereby deteriorating the quality of the subject foods and beverages.

Oxidative deterioration of foods and beverages involving browning generally causes problems in terms of both appearance and flavor. For instance, the organoleptic deterioration of beer is known to have a high degree of correlation with the concentration of dissolved oxygen in the beer. Thus, the duration of time in which brewed beer can be stored while retaining its high quality is dependent on how low the concentration of dissolved oxygen in beer can be maintained.

It has recently been shown by many studies that free radicals including active oxygen take part in the process of aging, cancer development and inflammation in mammals including the human being. Specific examples of active oxygen include superoxide anion radical ($O_2^-$), hydrogen peroxide ($H_2O_2$) and hydroxyradical ($OH_-$). These species are molecules of triplet oxygen with one, two or three electrons reduced, and singlet oxygen ($^1O_2$). All of them are highly reactive molecular species that damage nucleic acids and other cellular components and which hence are deleterious to human health. This problem has recently come into the spotlight as a result of successive publication of reports that show the presence of hydrogen peroxide in foods, beverages and various table luxuries. The source of ths hydrogen peroxide has been identified as dissolved oxygen by the present inventors (Suwa, Y. et al., "The Enzymatic Inactivation of Oxygen-Dependent Mutagenicity of Coffee" in Proc. 4th Intern. Conf. Environ. Mutagens, 262, 1985).

It would therefore be very important to remove oxygen from foods and beverages for the purpose of improving the organoleptic and other aspects of their quality and reducing their potential risk to human health. Prior Art:

Oxidases such as glucose oxidase and ascorbate oxidase are commonly employed as enzymes for removing oxygen from foods and beverages. The reaction scheme of deoxygenation by glucose oxidase is shown below, from which one can see that oxidases generate hydrogen peroxide via the superoxide anion ($O_2^-$), thereby causing problems not only to the quality control of foods and beverages of interest but also to the health of humans who ultimately consume them.

$$\beta\text{-D-glucose} + O_2 + H_2O \xrightarrow{\text{glucose oxidase}}$$

$$\text{D-gluconic acid} + H_2O_2$$

When a certain additive is employed to remove oxygen from foods and beverages, it is vitally important to ensure safety of not only the additive itself but also the product that is formed as a result of the deoxygenation reaction.

SUMMARY OF THE INVENTION

From these viewpoints, enzymes to be used as deoxygenators for foods and beverages are required to satisfy the following six conditions besides their deoxygenating capability:

(1) they should not cause any adverse effects on the organoleptic characteristics of the food or beverage of interest;

(2) they should be capable of retarding browning or other deterioration of the food or beverage not only in the short term but also for a long period of time;

(3) the food or beverage to be treated should contain a sufficient amount of substrate to perform the intended enzymatic reaction, or alternatively the necessary substrate can be incorporated in the food or beverage without causing any safety or organoleptic problems;

(4) no active oxgen such as superoxide anion radical ($O_2^-$) or hydrogen peroxide should be generated during the deoxygenation reaction;

(5) the deoxygenation reaction should be free from the generation of not only toxic substances but also reaction products having undesired physiological or pharmacological actions; and (6) the reaction time should be short enough to enable the completion of deoxygenation before the step of sterilization by retorting.

An object, therefore, of the present invention is to provide foods and beverages in which lactate monooxygenase that satisfies all of the six conditions described above is incorporated so as to prevent deterioration of their quality by causing oxygen to be eliminated therefrom rapidly and in a safe way.

Another object of the present invention is to provide a method of protecting foods and beverages against oxygenassociated deterioration in quality by incorporating lactate monooxygenase therein.

DETAILED DESCRIPTION OF THE INVENTION

With a view to finding an enzyme that satisfies the six conditions set forth above, the present inventors investigated many enzymes most of which were oxidases and oxygenases. At first, they were unable to locate a suitable enzyme. As already described, most of the oxidases including ascorbate oxidase and xanthine oxidase generate active oxygen and hence fail to satisfy condition (4). In addition, some oxidases were found to promote browning. Therefore, none of the oxidases tested were satisfactory. Even oxygenases were unsatisfactory since most of them failed to satisfy conditions (2), (3) and (5).

As a result of continued studies made to find the desired enzyme, the present inventors found unexpectedly that all of the six conditions under consideration could be satisfied by lactate monooxygenase (hereinafter abbreviated as LMO). The present invention has been accomplished on the basis of this finding.

Foods and beverages that are intended to be treated by the present invention include not only alcoholic beverages such as beer, sake, synthetic (compounded) sake, fruit wine, liqueurs, sweetened fruit wine and mirin (sweet sake used as seasoning), nonalcoholic beverages such as coffee, tea and oolong tea; fruit juice, fruit juice-containing beverages, milk and dairy products.

As shown by the following reaction scheme, LMO catalyzes the reaction of forming acetic acid, carbon dioxide and water from lactic acid and oxygen, thereby eliminating oxygen from the reaction solution:

(L-lactic acid)

$CH_3CH(OH)COOH + O_2 \rightarrow CH_3COOH + CO_2 + H_2O$.

The major advantage of LMO is that it is capable of fully preventing quality deterioration of foods and beverages by its deoxygenating action without affecting their organoleptic characteristics. Lactic acid which serves as a substrate for the enzymatic reaction is often present in the food or beverage of interest. For example, lactic acid was detected in concentrations of 20–110 ppm (measured as DLlactic acid and hereinafter the same) in beer, 310–607 ppm in sake of the second grade, and 532–652 ppm in ginjoshu (sake made from high polished rice). In consideration of the level of dissolved oxygen present in these kinds of alcoholic beverage (e.g., ca. 0.3–1.0 ppm in beer), the lactic acid present is sufficient for the enzymatic reaction to proceed even if it is not added externally. If necessary, lactic acid can be externally added without causing any safety problems. Its use as a food additive is approved in the Food Sanitation Act in Japan.

Besides lactic acid which serves as a substrate for LMO, the products of the reaction catalyzed by LMO are also safe. First of all, acetic acid is the major component of edible vinegar. Needless to say, both carbon dioxide and water are free from any safety problems. Even if lactic acid is present in large quantity, the concentration of dissolved oxygen which is the other substrate is present in an amount of at most about 9 ppm and becomes a rate-limiting factor for the reaction. Therefore, acetic acid will not be produced in a sufficiently high concentration to affect the flavor of the treated food or beverage.

In addition, as will be described later in this specification, LMO which is an emzyme needs to be used in a very small amount as compared with conventional deoxygenators such as vitamin C. Once the reaction has been completed, oxygen will not be restored since the reaction is irreversible in foods or beverages under sealed conditions. Therefore, canned or bottled foods or beverages can be sterilized by retorting without causing any problem of LMO inactivation.

In an attempt to maintain the freshness and flavor of fruit juice-containing beverages and oolong tea, the practice of using sterilized containers and caps and charging the contents aseptically at low temperatures (20°–25° C.) has been commercialized. Compared with the conventional full-charge method, this practice suffers a problem in that the contents are susceptible to accelerated oxidative deterioration on account of the large head space left in the container. The use of LMO is anticipated to become a great incentive to increased adoption by beverage manufacturers of the new aseptic charging and packaging technique which is intended to improve the quality and organoleptic characteristics of beverages.

LMO has an additional advantage in that it is capable of inhibiting the generation of hydrogen peroxide and other active oxygen species from foods and beverages. As discovered by the present inventors, active oxygen is derived from dissolved oxygen in foods and beverages, and LMO has the ability to eliminate dissolved oxygen which may be described as a precursor of active oxygen.

In the case of a beverage that needs sterilization with heat (i.e., retorting), LMO must be incorporated in the beverage for at least 30 minutes to 1 hour before retorting so that the necessary reaction time is ensured after the beverage is filled into a bottle or can. The shorter the reaction time, the greater the amount of LMO that must be incorporated. With beverages that need not be retorted such as draft beer and fresh juice, LMO may be added at any stage that preceeds the step of charging into the container. Preferably, LMO is incorporated in beverages during or immediately before their charging into the container. In other words, the beverages in which LMO has been incorporated under aerobic conditions should not be left to stand for an unduly long time.

The amount of LMO to be added varies greatly depending on the temperature of the beverage into which LMO is to be incorporated, its pH, the concentration of dissolved oxygen or L-lactic acid, the reaction time and the concentration of reaction inhibitors. Satisfactory results in oxygen removal are normally attained by incorporating 0.001–1 unit, preferably 0.01–0.5 units, of LMO per ml of the beverage.

If a beverage to be treated contains no L-lactic acid at all, LMO will not exhibit its deoxygenating action unless L-lactic acid is added to the beverage. Theoretically, L-lactic acid need not be present or added in a molar amount larger than that of the dissolved oxygen. In practice, however, since the beverage being charged into the container contains only less than a few pm of dissolved oxygen, the presence of L-lactic acid at an equimolar amount is insufficient to ensure rapid deoxygenation reaction by LMO. For example, the addition of L-lactic acid in an molar amount equal to said low amount of dissolved oxygen will normally produce a rate of deoxygenation only as low as 0.005 ppm/h or below in the presence of LMO added at about 0.01 unit/ml. Therefore, L-lactic acid is preferably added to attain an approximate concentration of 10-300 ppm, most preferably 50 ppm, in which case about 0.01 unit/ml of LMO is sufficient to reduce the concentration of dissolved oxygen to a practically satisfactory level (in most cases zero).

The ability of LMO to reduce the concentration of dissolved oxygen is described hereinafter in detail with reference to experimental data. The reagents employed in the experiments described below were purchased from Wako Pure Chemical Industries, Ltd. (Osaka) while the foods and beverages tested were purchased from retail stores in Osaka City.

LMO was isolated and purified from *Mycobacterium phlei* (IFO 3158 or IFO 13160) or *M. smegmatis* (IFO 13167). The microorganisms were cultivated and the enzyme purified by the method of Takemori et al., (Takemori, S. et al.; J. Biol. Chem., Vol. 243(2), 313-319, 1968).

The activity of the LMO prepared was calculated from the measurement of oxygen consumption at 25° C. with lithium L-lactate used as a substrate. Oxygen consumption was measured with a dissolved oxygen electrode (Oriental Electric Co., Ltd., Saitama), with a reaction cell being charged with a predetermined amount of the sample, 72 $\mu$mol of a phosphate buffer solution (pH, 6.0) and 270 $\mu$mol of lithium L-lactate to make a total volume of 3.6 ml. One unit of enzymatic activity is equated by the amount of enzyme that consumed 1 $\mu$mol of oxygen per minute under the conditions of measurement described above.

Test Method (i) Measuring the Concentration of Dissolved Oxygen

In order to measure the rate of oxygen removal by LMO, the sample beverage was first placed in a reaction vessel for oxygen measurement (Type BOM-11 of Ishikawa Seisakusho, Ltd., Tokyo) so that it would be isolated from the ambient air. Then, a predetermined amount of LMO was added to the sample with stirring and the decrease in concentration of dissolved oxygen was measured with the dissolved oxygen electrode (type DG-5 of Ishikawa Seisakusho, Ltd., Tokyo).

The concentration of dissolved oxygen in the untreated beverage had been measured with Model 26073 of Orbisphere Corporation, Switzerland.

(ii) Measuring Anti-Browning Effects

A beverage sample incorporating a predetermined amount of LMO was charged into a container and placed in an incubator at 50° C., which was adjusted to create conditions that would cause accelerated browning. Sampling was made at given time intervals and the following measurement was conducted: 3 ml of the beverage sample was mixed with an equal amount of 99.5% ethyl alcohol for 1 minute; the mixture was filtered through filter paper (TOYO No. 2: Toyo Roshi Kaisha, Tokyo); and the absorption of the filtrate at 400 nm was measured. The ability of LMO to inhibit browning was evaluated against an LMO-free control beverage.

(iii) Organoleptic Test

LMO-containing beverage samples were subjected to an organoleptic test by a three-point preference test wherein panelists compare three samples at a time as described in S. Sato, "Introduction to Organoleptic Test", p. 58, published by Nikkagiren, Tokyo 1978. Significance in differentiation is first tested; if the significance is verified, then, the order in preference between samples is determined from the collected ratings given by the panelists who correctly differentiated between the test samples.

(iv) Test For Inhibiting the Growth of Aerobic Microorganism

Using strain *Bacillus subtilis* H17 as a test microorganism, the ability of LMO to inhibit the growth of this strain was investigated by a liquid culture method. A test medium (for its composition, see Table 1) containing 1 mg/ml of L-lactic acid was inoculated with *B. subtilis* in a concentration of ca. $1 \times 10^6$ ml, and a predetermined amount of LMO was thereafter added.

TABLE 1

| Composition of Test Medium | |
|---|---|
| Ingredients | Amount (per l) |
| Polypeptone | 10 g |
| Yeast extract | 10 g |
| Glucose | 10 g |
| K$_2$HPO$_4$ | 3 g |
| L—lactic acid (Li salt) | 1 g |

The pre-culture of *B. subtilis* on the test medium was diluted to a predetermined concentration of 2.0 ml of this dilution was poured into a vial (capacity of 8.4 ml) closed with a highly hermetic screw cap. Following stationary culture at 37° C. for 48 hours, the absorption at 660 nm was measured and the ability of LMO to inhibit microbial growth was evaluated by comparison with the culture of an LMO-free control sample.

(v) Test For Inhibiting the Oxidation of Ascorbic Acid

The ability of LMO to inhibit the oxidation of L-ascorbic acid as an antioxidant or as a vitamin was tested on the basis of determination of L-ascorbic acid by the hydrazine method [i.e., DNP method described by Roe, J. J. H. et al. in J. Biol. Chem., Vol. 174, 201-208 (1948, and by Arakawa, N. et al. in Vitamins (Japan), Vol. 56 (5, 6), 255-262 (1982)].

(vi) Measuring the Concentration of Hydrogen Peroxide

In order to investigate the ability of LMO to inhibit the generation of active oxygen, the concentration of hydrogen peroxide in a beverage sample was measured by the following procedures.

Hydrogen peroxide measurement was conducted with Oridetector Model III (Oriental Electric Co., Ltd., Saitama). A beverage sample containing predetermined amounts of LMO and sodium lactate was put into a reaction cell for oxygen measurement and isolated from the ambient air, followed by addition of catalase (made from bovine liver by Pharmacia P-L Biochemicals, Inc.) in an amount of 1,500 units/10 $\mu$l with stirring in a nitrogen stream. The amount of oxygen that was generated by decomposition of hydrogen peroxide was measured with a dissolved oxygen electrode. The concentration of hydrogen peroxide was calculated from the quantity of dissolved oxygen that had been generated in accordance with following reaction scheme:

Results

(i) Deoxygenating Activity of LMO in Various Beverages

LMO was added to various beverage samples and its deoxygenating activity was determined. The results are shown in Table 2. The deoxygenating activity is expressed in terms of the quantity of oxygen removed per hour at 25° C. The data in Table 2 shows that LMO was capable of removing effective amounts of dissolved oxygen from the various beverage samples tested. In the experiment, LMO was added in comparatively large amounts in order to ensure that significant deoxygenating effects would develop within one hour after the addition of LMO. Depending on the beverage tested, sodium lactate was also added. In practice, however, deoxygenation need not be completed within one hour in all cases in order to attain the intended effects and it has been shown that with common bottled or canned beverages, deterioration of their quality including organoleptic characteristics can be prevented by removing dissolved oxygen within 24 hours from charging the contents into bottles or cans and sealing them. Therefore, it should be noted that effects beneficial for practical purposes can be attained by incorporating LMO in concentrations lower than 0.078 units/ml which is the value employed in the experiment the results of which are shown in Table 2. The same comments apply to lactate and effects that are satisfactory for practical purposes can be attained by adding it in very low concentrations (10–200 ppm as a final value) or even if it is not added at all.

TABLE 2

| Beverage | Deoxygenating Activity of LMO in Various Beverages | | |
|---|---|---|---|
| | Concentration of dissolved oxygen* before addition of LMO** (ppm) | Amount of sodium lactate added (% w/v) | Rate of deoxygenation (ppm/h) |
| Lactobacillus containing beverage | | | |
| Brand A | 6.38 | 0 | 19.2 |
| Brand B | 7.75 | 0 | 38.6 |
| Brand C | 3.29 | 0 | 68.3 |
| Coffee | | | |
| Brand D | 0.90 | 0 | 10.9 |
| Brand E | 1.12 | 0.01 | 12.4 |
| Fruit juice containing beverage | | | |
| Brand F (50% orange juice) | 1.18 | 0.1 | 6.1 |
| Brand G (100% orange juice) | 2.04 | 0.1 | 2.6 |
| Brand H (100% apple juice) | 2.18 | 0.1 | 40.0 |
| Brand I (100% tomato juice) | 1.74 | 0.1 | 40.0 |
| Beer | | | |
| Brand J (Draft beer) | 4.90 | 0.1 | 3.3 |
| Sake | | | |
| Brand K (First grade) | 8.14 | 0 | 3.9 |

*With beverages such as beer that had low concentrations of dissolved oxygen, the oxygen concentration was artificially raised by stirring before determining the rate of deoxygenation.
**With all beverages tested, LMO was added to give a final concentration of 0.078 units/ml.

Figure 1:
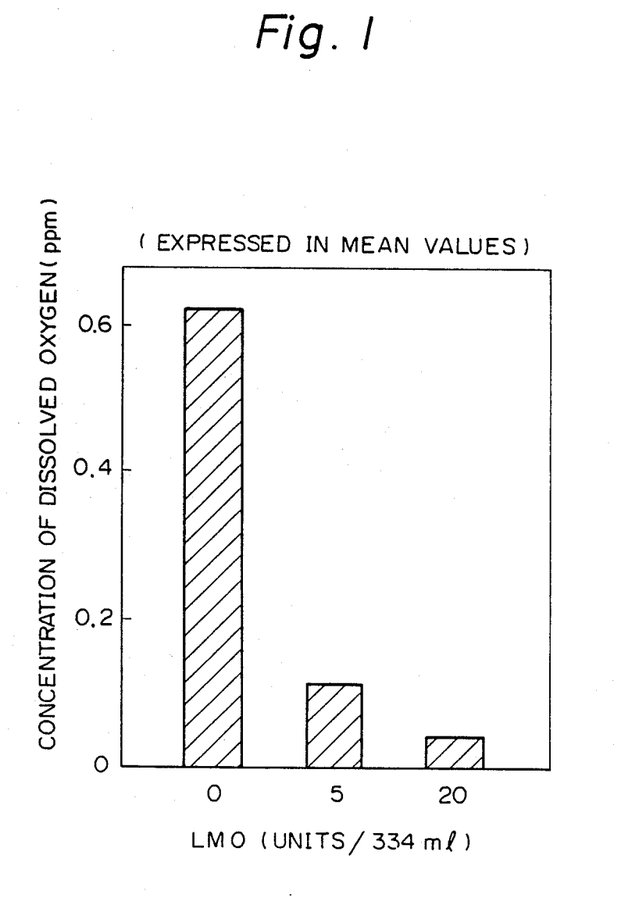
FIG. 1 is a graph showing the deoxygenating ability of lactate monooxygenase in beer.

FIG. 1 shows the deoxygenating activity of LMO in beer under practical conditions. In the experiment, groups of draft beer each consisting of five small bottles (334 ml) were treated with LMO which was added after opening the bottles. Thereafter, in order to prevent the occurrence of errors in measurement, the head space in each bottle was filled with beer that had been stirred overnight at 4° C. The bottles were then closed with a cap and left to stand overnight at 28° C. before measuring the concentration of dissolved oxygen. In the LMO-free control, dissolved oxygen was detected in an amount of $0.601\pm0.05$ ppm, (mean±S.D.). By addition of LMO in 5 units per bottle, the concentration of dissolved oxygen was reduced to $0.122\pm0.036$ ppm. Further reduction was accomplished by adding 20 units of LMO per bottle ($0.044\pm0.019$ ppm).

(ii) Organoleptic Test

Bottles (334 ml) of draft beer containing 20 units of LMO per bottle were evaluated organoleptically by comparison with an LMO-free control. The organoleptic test was conducted by the three-point preference test as already described. To the LMO-containing samples, sodium lactate was also added in an amount of 100 ppm (final concentration). All samples under test were left to stand at 28° C. for 3 months.

The organoleptic test was performed by the following procedures: significance in differentiation was first tested and the answers given by panelists who correctly differentiated the LMO-containing sample from the control were collected to check which of the LMO-containing sample and the control they preferred.

Of the 30 panelists who participated in the test, 25 persons correctly differentiated the LMO-containing sample from the control, indicating that the distinction between the two was significant ($P \leq 5\%$). Of the 25 panelists who gave the correct answer, 6 people preferred the control (LMO-free beer) to the LMO-containing sample and the remaining 19 persons preferred the LMO-containing sample. The LMO-containing beer was preferred with significant difference ($p \leq 5\%$). The panelists who preferred the LMO-containing beer made comments that they liked this beer because it was "refreshing", "free from undersirably long-lasting bitterness", "fresh" and "devoid of unpleasant taste", all of these reasons being based on organoleptic evaluation that reflected the inherent characteristics of beer. On the other hand, most of the panelists who disliked the LMO-free beer commented that it "had an unpleasant taste" or that they "sensed deterioration", clearly reflecting the deterioration in quality of this beer.

(iii) Inhibition of the Growth of Aerobic Bacterium by LMO

Figure 2:
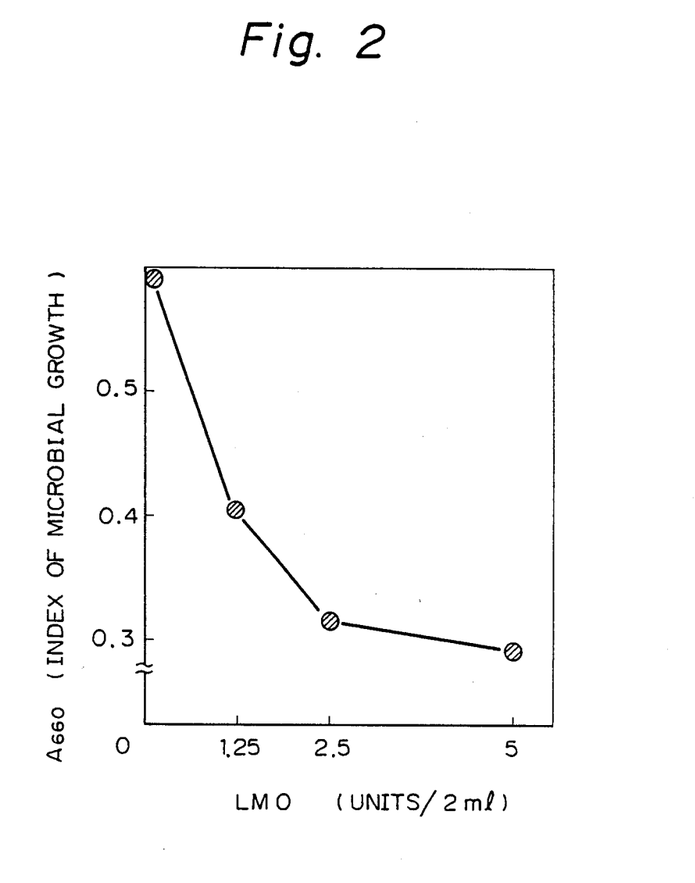
FIG. 2 is a graph showing the ability of lactate monooxygenase to inhibit the growth of *B. subtilis*.

Using *Bacillus subtilis* strain H17 as an aerobic bacterium, the microbial growth inhibiting activity of LMO was examined by the already described test method (iv). The results are shown in FIG. 2, from which one can see that LMO was highly effective in inhibiting the growth of *B. subtilis* strain H17. This effectiveness of LMO is most probably due to the reaction that was catalyzed by LMO and which involved dissolved oxygen as a substrate.

(iv) Inhibition of Browning by LMO

Figure 3:
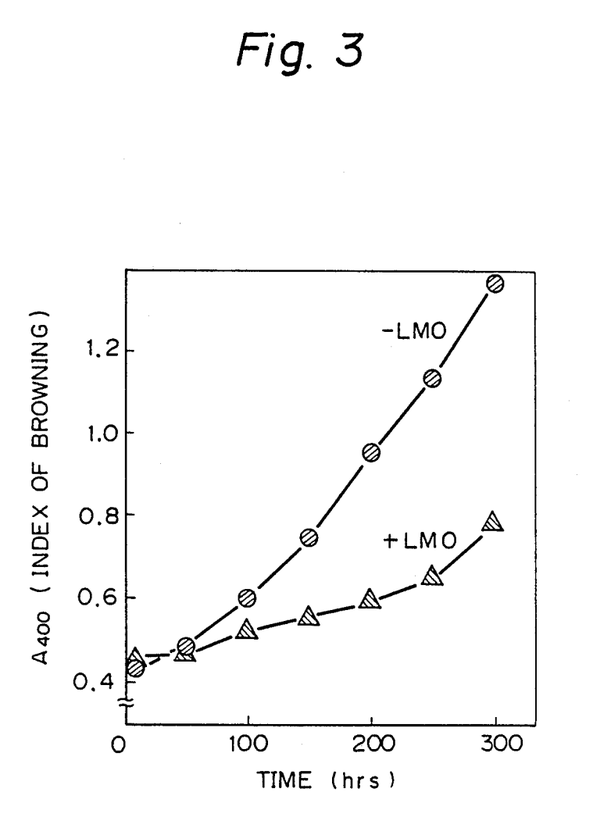
FIG. 3 is a graph showing the ability of lactate monooxygenase to retard browning of a fruit juice-containing beverage.

The ability of LMO to inhibit the browning of a sample of commerical 100% grapefruit juice was investigated by the already-described test method (ii). The results are shown in FIG. 3, from which one can see that compared with the LMO-free juice (control), the sample containing 1 unit of LMO per ml obviously experienced a small degree of browning, indicating the effectiveness of LMO against browning.

(v) Inhibition of Oxidation of L-ascorbic Acid by LMO

Figure 4:
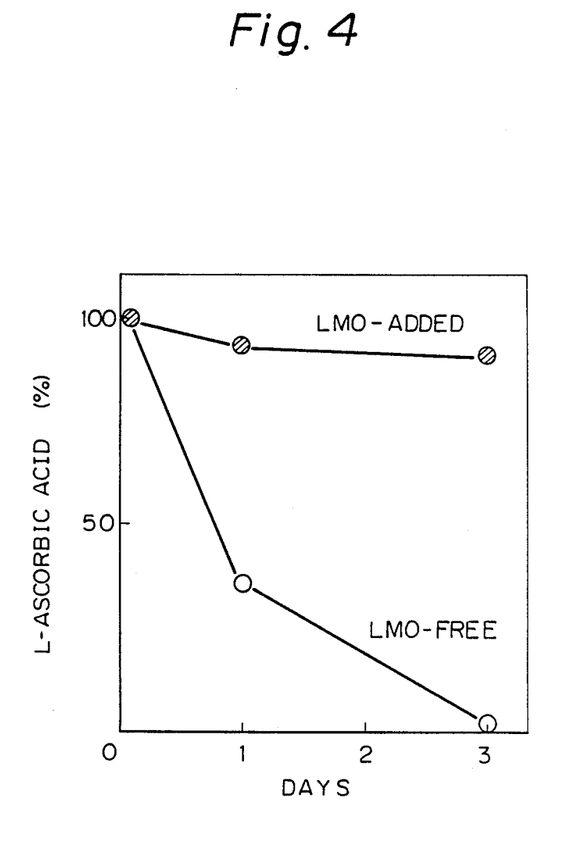
FIG. 4 is a graph showing the ability of lactate monooxygenase to prevent oxidation of L-ascorbic acid.

The ability of LMO to inhibit the oxidation of L-ascorbic acid (reduced vitamin C) was investigated by the already-described test method (v). A total of 3.5 ml of solution consisting of 0.1 ml of L-ascorbic acid (6.6 mg/ml), 2.9 ml of 0.1% sodium lactate and 0.5 ml of a predetermined unit of LMO was put into a vial (capacity, 8.4 ml) closed with a highly hermetic screw cap and stored at 30° C. At given time intervals, the amount of residual L-ascorbic acid was determined by the hydrazine method.

The results were shown in FIG. 4, from which one can see that L-ascorbic acid in the LMO-free control solution was completely oxidized in 3 days whereas more than 90% of the ascorbic acid remained in the LMO-containing sample solution even on the third day of storage. In this test, too, LMO have prevented the oxidation of L-ascorbic acid by eliminating dissolved oxygen.

The present invention is hereinafter described in greater detail with reference to examples of LMO-containing beverages. It should, however, be noted that the scope of the present invention is by no means limited to these examples.

EXAMPLE 1

Canned Coffee

The term "canned coffee" as used herein includes coffee beverages, coffee-containing refreshing beverages, and coffee with milk. A formulation of coffee beverage is shown below.

| | |
|---|---|
| Roasted coffee beans (in terms of green beans) | 10 g |
| Raw powdered milk | 1.6 g |
| Skimmed powdered milk | 1.7 g |
| Sugar | 18.75 g |
| Sodium bicarbonate | 0.25 g |
| LMO | 16 units |
| Water to make | 250.0 g |

EXAMPLE 2

Oolong Tea

| | |
|---|---|
| Oolong tea (fresh commercial product) | 1,500 ml |
| DL-lactic acid | 120 mg |
| LMO | 100 units |

EXAMPLE 3

Mandarine Orange Juice

| | |
|---|---|
| 1/6 Frozen concentrate of mandarine orange ("Unshu") juice (Bx, 54) | 173 g |
| DL-sodium lactate | 0.2 g |
| LMO | 80 units |
| Water to make | 1,000 ml |

EXAMPLE 4

50% Mandarine Orange Juice

| | |
|---|---|
| 1/6 Frozen concentrate of mandarine orange ("Unshu") juice (Bx, 54) | 88 g |
| Sugar | 83 g |
| Citric acid | 2 g |
| Flavor | 2 ml |
| DL-sodium lactate | 0.13 g |
| LMO | 100 units |
| Water to make | 1,000 ml |

EXAMPLE 5

Apple Juice

| | |
|---|---|
| 100% apple juice | 180 ml |
| LMO | 8 units |

EXAMPLE 6

Orange Juice

| | |
|---|---|
| 100% orange juice ("Valencia") | 180 ml |
| LMO | 20 units |

EXAMPLE 7

Synthetic (Compounded Sake)

| | |
|---|---|
| 30% alcohol | 6,750 ml |
| 70% glucose | 580 g |
| Syrup | 60 g |
| Saccinic acid | 10 g |
| 75% lactic acid | 4 g |
| Sodium glutamate | 2.2 g |
| Sodium chloride | 2.2 g |
| Water | 2,500 ml |
| LMO | 400 units |

EXAMPLE 8

Sake

| | |
|---|---|
| Sake of the first grade (with alcohol content of 15%) | 1,800 ml |

-continued

| | |
|---|---|
| LMO | 110 units |

EXAMPLE 9

Beer A

| | |
|---|---|
| Beer (bottom fermented pale-colored beer with 4.5% alcohol) | 633 ml |
| LMO | 36 units |

EXAMPLE 10

Beer B

| | |
|---|---|
| Beer (top fermented dark-colored stout beer with 7.2% alcohol) | 330 ml |
| LMO | 27 units |

As described on the foregoing pages, the present invention provides a method by which oxygen-related deterioration in the quality of foods and beverages can be prevented in a safe and simple way. Foods and beverages treated by this method retain a good flavor for a prolonged period without forming any product of deterioration that is potentially harmful to the health of human beings.

What is claimed is:

1. A food or beverage having improved resistance to oxygen-related deterioration, which comprises a food or beverage susceptible to said deterioration mixed with lactate monooxygenase in an amount effective for improving said resistance.

2. A food or beverage according to claim 1, wherein the lactate monooxygenase is lactate 2-monooxygenase (EC 1.13.12.4).

3. A food or beverage according to claim 1, which is selected from the group consisting of alcoholic beverages, fruit juice, fruit juice-containing beverages; coffee; tea; milk and dairy products.

4. A food or beverage according to claim 1, wherein the lactate monooxygenase is present in an amount of 0.001-1 unit/ml.

5. A food or beverage according to claim 1, which is packed in a sealed container.

6. A method which comprises adding lactate monooxygenase to a food or beverage susceptible to oxygen-related deterioration in an amount sufficient to protect said food or beverage against said deterioration.

7. A method according to claim 6, wherein the lactate monooxygenase is lactate 2-monooxygenase (EC 1.13.12.4).

8. A method according to claim 6, wherein the food or beverage is selected from the group consisting of alcoholic beverages, fruit juice, fruit juice-containing beverages; coffee; tea; milk and dairy products.

9. A method according to claim 6, wherein the lactate monooxygenase is incorporated in an amount of 0.001-1 unit/ml.

10. A method according to claim 6, wherein the food or beverage is packed in a sealed container.

11. A method according to any one of claims 6-10, wherein L-lactic acid is also added to said food or beverage.

* * * * *